United States Patent [19]
Weaver et al.

[11] Patent Number: 5,993,809
[45] Date of Patent: Nov. 30, 1999

[54] LYSOZYME FUSION PROTEINS IN INFECTIONS

[75] Inventors: Timothy Edward Weaver, Loveland; Henry Toyin Akinbi, Cincinnati, both of Ohio

[73] Assignee: Children's Hospital Medical Center, Cincinnati, Ohio

[21] Appl. No.: 09/193,877

[22] Filed: Nov. 18, 1998

[51] Int. Cl.[6] .......................... A61K 38/16; A61K 38/43; A61K 38/47
[52] U.S. Cl. ..................... 424/94.61; 435/206; 435/69.1; 514/12; 530/350
[58] Field of Search ............................. 530/350; 514/12; 424/94.61; 435/206, 69.1

[56] References Cited

PUBLICATIONS

Dobbs et al., An Improved Method of Isolating Type II Cells in High Yield and Purity, Am Rev Respir Dis 134:141–145 (1986).

Konstan et al., Comparative Study of Lysozyme and Its Secretion By Tracheal Epithelium, Experimental Lung Research 3:175–181 (1982).

Glick et al., Degradation of Group A Streptococcal Cell Walls by Egg–White Lysozyme and Human Lysosomal Enzymes, Infection and Immunity, Sep. 1972, vol. 6, No. 3, pp. 403–413.

Yeh et al., Evolution of Rodent Lysozymes, Isolation and Sequence of the Rat Lysozyme Genes, Molecular Phylogenetics and Evolution, vol. 2, No. 1, Mar., pp. 65–75. (1993).

Konstan et al., Human Lung Lysozyme: Sources and Properties, Am Rev Respir Dis 1981: 123:120–124.

Chirgwin, et al., Isolation of Biologically Active Ribonucleic Acid from Sources Enriched in Ribonuclease, Biochemistry, vol. 18, pp. 5294–5299. (1979).

Murphy, S. and Florman, A.L., Lung Defenses Against Infection: A Clinical Correlation, Pediatrics, vol. 72, No. 1, Jul. 1983, pp. 1–15.

Gordon et al., Modulation of Neutrophil Function by Lysozyme, J. Clin. Invest. vol. 64, Jul. 1979, pp. 226–232.

Aviv et al., Purification of Biologically Active Globin Messenger RNA by Chromatography on Oligothymidylic acid–Cellulose, Proc. Nat'l Acad. Sci. USA, vol. 69, pp. 1408–1412. (1972).

Widdicombe, J., Relationships among the Composition of Mucus, Epithelial Lining Liquid, and Adhesion of Microorganisms, Am J Respir Crit Care Med, vol. 151, 1995, pp. 2088–2093.

Akinbi et al., Rescue of SP–B Knockout Mice with a Truncated SP–B Proprotein, Journal of Biological Chemistry, vol. 272, No. 15, pp. 9640–9647, 1997.

Lin et al., Structural Requirements for Targeting of Surfactant Protein B (SP–B) to Secretory Granules in Vitro and in Vivo, The Journal of Biological Chemistry, vol. 271, No. 33, pp. 19689–19695, 1996.

Lin et al., Structural requirements for intracellular transport of pulmonary surfactant protein B (SP–B), Biochimica et Biophysica Acta 1312 (1996) pp. 177–185.

Hill, I. R. and Porter, P., Studies of Bactericidal Activity to *Escherichia coli* of Porcine Serum and Colostral Immunoglobulins and the Role of Lysozyme with Secretory IgA, Immunology, 1974, 26, pp. 1239–1250.

Stephan W. Glasser, Thomas R. Korhagen, Timothy Weaver, Tami Pilot–Mattias, J. Lawrence Fox, and Jeffrey A. Whitsett, cDNA and deduced amino acid sequence of human pulmonary surfactant–associated proteolpid SPL (Phe), Pro. Natl. Acad, Sci. USA, vol. 84, pp. 4007–4011, Jun. 1987.

*Primary Examiner*—Michael P. Woodward
*Assistant Examiner*—Michael Borin
*Attorney, Agent, or Firm*—Wood, Herron & Evans, L.L.P.

[57] ABSTRACT

A method and composition for prophylaxis and/or treatment of bacterial infections, particularly bacterial respiratory infections. A fusion protein of lysozyme and the carboxyl terminal propeptide of surfactant protein-B (SP-B) with the preceding ten amino acids of the mature SP-B peptide is administered in a pharmaceutically acceptable medium to an individual. The fusion protein may be selected so as to deliver it to a target infection site, such as the lungs or gastrointestinal tract. The method and composition eliminates problems associated with conventional antibiotic treatments, such as inefficacy and promotion of antibiotic resistant bacterial strains.

12 Claims, 1 Drawing Sheet

LYSOZYME FUSION PROTEINS IN INFECTIONS

The U.S. Government has a paid-up license in this invention and the right in limited circumstances to require the patent owner to license others on reasonable terms as provided for by the terms of Grant nos. R01-HL56285 and HL56285S award by the National Institutes of Health.

FIELD OF THE INVENTION

The invention relates to prophylactic and therapeutic uses of a lysozyme/surfactant protein-B fusion protein in bacterial infections.

BACKGROUND OF THE INVENTION

Bacterial infections remain a leading cause of worldwide morbidity and mortality. While antibiotics are often safe and efficacious, there is widespread concern over bacterial strains that have become resistant to classic antibiotic treatment regimens. In individuals infected with resistant strains, antibiotic administration results in incomplete and ineffective treatment necessitating additional treatment along with propagation of the resistant strains. Preventative measures and alternative treatments that do not rely on antibiotics are therefore desirable.

The respiratory and gastrointestinal tracts are frequent sites of bacterial infections in normal individuals. The normal respiratory tract has natural clearance mechanisms that help to prevent bacterial colonization. These mechanisms include the presence of a mucus gel that acts as a barrier to bacterial invasion, the propulsive forces of the cilia on the epithelial lining of the airways, and the secretion of antibacterial humoral factors such as the secretory immunoglobulins IgA and IgM, the proteins lactoferrin, betalysin and fibronectin, complement components and the enzyme lysozyme. Of these antimicrobial factors, lysozyme is the best established antimicrobial substance in airway secretions.

In certain individuals such as those who are immunocompromised, who are in less than optimal health, who lack fully functional immune systems such as neonates or geriatric patients, or who suffer from a disease affecting the respiratory tract such as cystic fibrosis or the gastrointestinal tract such as ulcerative colitis or sprue, bacterial infections may have severe consequences leading to serious illness or even death. For example, production of altered mucus in cystic fibrosis patients leads to dilation of the exocrine ducts, destruction of acinar tissue, and replacement of the destroyed tissue by fibrous connective tissue. Involvement of the lungs leads to pneumonia and bronchiectasis. The paucity of systemic dissemination of infection in these patients, even in the presence of substantial bacterial colonization of the lungs, indicates that their systemic immunity is essentially intact, yet they are susceptible to pulmonary infections. These patients often die in their teens or early twenties from terminal lung infections in spite of aggressive antibiotic therapy.

Human lysozyme is an naturally occurring enzyme that is known to exhibit bactericidal activity in vitro and thus would appear to be a promising way to prevent and/or treat bacterial infections. Lysozyme is a small (15 kilodaltons), basic protein that is produced in most tissues. It is secreted and is present in most body secretions such as mucus. In the lungs, immunohistochemical methods have localized lysozyme to the bronchial serous submucosal glands, alveolar macrophages and lamellar bodies in Type II alveolar epithelial cells. Approximately 80% of lysozyme secreted into the airway comes from the mucosal layer of the upper airways.

In vitro, lysozyme has been demonstrated to act independently to cause bacterial death. It is known that one way lysozyme kills bacteria is by hydrolyzing the glycosidic bond between C-1 of N-acetylmuramic acid and C-4 of N-acetylglucosamine in the bacterial polysaccharide cell wall. Lysozyme can also kill bacteria by acting synergistically with other proteins such as complement or antibody to lyse bacterial cells. Lysozyme, produced by polymorphonuclear leukocytes such as neutrophils, inhibits chemotaxis of polymorphonuclear leukocytes and limits the production of oxygen free radicals following an infection. This limits the degree of inflammation, while at the same time enhances phagocytosis by these cells. Lysozyme is also probably involved in the response of airway tissue to injury.

While the antibacterial effects of lysozyme in vitro have been well documented, there has heretofore been no way to exploit these effects of lysozyme for in vivo use. Previous reports furthermore implied that sustained lysozyme administration would be harmful.

Surfactant protein-B (SP-B) is one of the protein components of pulmonary surfactant. Pulmonary surfactant, a complex mixture of phospholipids and proteins, is synthesized and secreted by alveolar type II epithelial cells, a specialized exocrine cell. Normal respiratory function requires pulmonary surfactant for maintenance of alveolar patency.

A method and composition for the prophylaxis and/or treatment of bacterial infections, particularly respiratory bacterial infections as frequently occurs in patients with cystic fibrosis, is thus desirable.

SUMMARY OF THE INVENTION

This invention is directed to a composition for the prophylaxis or treatment of a bacterial infection in a mammal. The composition is either a lysozyme/surfactant protein-B (SP-B) fusion protein SEQ ID NO:3 (rat lysozyme SEQ ID NO:1 fused with the carboxyl terminal SP-B propeptide and the preceding ten amino acids of the mature SP-B peptide SEQ ID NO:4), or a lysozyme/SP-B fusion protein SEQ ID NO:6 (human lysozyme SEQ ID NO:5 fused with the carboxyl terminal SP-B propeptide and the preceding ten amino acids of the mature SP-B peptide SEQ ID NO:4). The composition prevents or treats a respiratory infection such as occurs frequently in individuals with cystic fibrosis, or a gastrointestinal infection.

The invention is also directed to a method of preventing or treating a bacterial infection in a mammal by administering a lysozyme/SP-B fusion protein SEQ ID NO:3 or SEQ ID NO:6 in a pharmaceutically acceptable composition in a dosing regimen sufficient to prevent or treat the infection. The route of administration may be parenteral, for example by inhalation, or nonparenteral.

The invention is still further directed to a fusion protein SEQ ID NO:3, comprising a rat lysozyme SEQ ID NO:1 and a carboxyl terminal SP-B propeptide with the ten terminal amino acids of the mature peptide SEQ ID NO:4, having antibacterial activity in a mammal.

The invention is still further directed to a fusion protein SEQ ID NO:6, comprising a rat lysozyme SEQ ID NO:5 and a carboxyl terminal SP-B propeptide with the ten terminal amino acids of the mature peptide SEQ ID NO:4, having antibacterial activity in a mammal.

The invention is additionally directed to a method of treating a bacterial respiratory infection in an individual having cystic fibrosis by administering a lysozyme/SP-B fusion protein SEQ ID NO:3 or SEQ ID NO:6 to the individual. The fusion protein may be administered by aerosol installation.

These and other methods and compositions will be apparent in light of the following FIGURE and detailed description.

DETAILED DESCRIPTION OF THE PREFERRED EMBODIMENT

Preparation of Fusion Protein

Rat lysozyme is a hydrophobic peptide of 148 amino acids SEQ ID NO:1. Human lysozyme SEQ ID NO:5 also has 148 amino acids and has 69% homology with rat lysozyme.

Surfactant protein-B (SP-B) is a hydrophobic peptide of 79 amino acids that avidly associates with surfactant phospholipids in the alveolar airspace. Human SP-B is synthesized by alveolar type II epithelial cell as a prepropeptide of 381 amino acids SEQ ID NO:2. Mature SP-B is generated by sequential cleavage of a 23 amino acid signal peptide, an amino terminal (N-terminal) propeptide of 177 amino acids, and a carboxyl terminal (C-terminal) propeptide of 102 amino acids. The C-terminal propeptide has been shown to function in maintenance of the size of lamellar bodies which store SP-B and in determining the intracellular surfactant pool size.

Complementary DNA (cDNA) corresponding to rat lysozyme and human SP-B was synthesized. The protocol used for synthesis was that described in Akinbi et al., J. Biol. Chem. 1997; 272: 9640–9647, which is expressly incorporated by reference herein in its entirety. Complementary DNA to rat lysozyme was generated as follows. Alveolar Type II epithelial cells were isolated from adult rat lung as described by Dobbs, et al., An improved method for isolating Type II cells in high yield and purity, Am. Rev. Respir. Dis. 134:140–145, 1986). Total RNA was isolated from Type II cells by the method of Chirgwin, et al., The isolation of biologically active ribonucleic acid from sources enriched in ribonuclease, Biochemistry 18:5294–5299, 1979) and polyA+ RNA by the method of Aviv and Leder, Purification of biologically active globin messenger RNA by chromatography on oligothymidylic acid-cellulose, Proc. Nati. Acad. Sci. USA 69:1408–1412, 1972. Single stranded cDNA, generated from isolated polyA30 RNA with reverse transcriptase (Maniatis, et al. *Molecular Cloning: A Laboratory Manual*, Cold Spring Harbor Laboratory, Cold Spring Harbor, N.Y. 1982), was used as a template for PCR amplification of the entire coding sequence of lysozyme using oligonucleotide primers based on the published sequence of the rat enzyme by Yeh, et al. Evolution of rodent lysozymes: Isolation and sequence of the rat lysozyme genes, Mol. Physiol. Evol. 2:25–75, 1993. Isolation of the human SP-B cDNA has previously been described (Glasser, S. W., et al. cDNA and deduced amino acid sequence of human pulmonary surfactant-associated proteolipid SPL (Phe)., Proc. Natl. Acad. Sci. USA 84:4007–4011, 1987).

The synthesized cDNAs were generated into a chimeric molecule consisting of the rat lysozyme protein and a carboxyl terminal (C-terminal) propeptide of a human surfactant protein B (SP-B). Specifically, this chimeric molecule was a fusion protein of residues 1–148 of rat lysozyme SEQ ID NO:1 and residues 270–381 of SEQ ID NO:2, shown in SEQ ID NO:4, forming a lysozyme/surfactant-B fusion protein SEQ ID NO:3.

Preparation of Transgenic Mice

Three lines of transgenic mice were generated that expressed a cDNA construct comprising the entire coding sequence for rat lysozyme SEQ ID NO:1 and the entire C-terminal propeptide of SP-B along with the preceding ten amino acids from the C-terminal of the mature peptide SEQ ID NO:4. The coding sequence for rat lysozyme SEQ ID NO:1 was cloned in frame with the coding sequence for the C-terminal propeptide and preceding 10 amino acids for human pulmonary surfactant protein B propeptide SEQ ID NO:4. FVB/N transgenic mice expressing a transgene construct encoding the fusion protein SEQ ID NO:3 under the control of the 3.7- kilobase (kb) human surfactant protein C (SP-C) promoter were generated as described in Lin et al. (J. Biol. Chem. 1996; 271: 19689–19695) which is expressly incorporated by reference herein in its entirety. The expression of transgene RNA in these mice was restricted to the distal respiratory epithelium.

Expression of the chimeric protein SEQ ID NO:3 was confirmed by Western blot analysis, as is known to one skilled in the art using antibody #R961 89, generated and characterized as reported by Lin, et al., Structural requirements for intracellular transport of pulmonary surfactant protein B (SP-B). Biochim. Biophys. Acta Mol. Cell. Res. 1312:177–185, 1996.), that detects the C-terminal propeptide of SP-B proprotein. A protein of approximately 29 kDa was detected in transgenic mice by using this antibody, as would be predicted by the size of the construct of 15 kDa rat lysozyme and 14 kDa C-terminal propeptide and preceding 10 amino acids SEQ ID NO:3. The transgene product was detected in both lung homogenates and in bronchoalveolar lavage fluids, consistent with secretion of the chimeric protein SEQ ID NO:3 into the alveolar space. Constitutive expression of the chimeric protein SEQ ID NO:3 was not associated with altered lung structure, as assessed by light microscopy evaluation of lung tissue stained with hematoxylin and eosin.

Efficacy of Fusion Protein

Five week old transgenic mice (n=56) carrying the fusion protein SEQ ID NO:3 (treated) and their wild type litter mates (control) were infected with $10^6$ strain IIII group B streptococci (GBS) via intratracheal administration. Aliquots of GBS were grown in Todd Hewitt broth at 37° C. overnight and bacteria were pelleted by centrifugation. The bacterial pellet was suspended in sterile phosphate buffered saline (PBS) at a concentration of $10^7$/ml. One hundred microliters of bacterial suspension ($10^6$ bacteria) were drawn into tuberculin syringes fitted with 27 gauge needles in preparation for the intratracheal injection. All injections were carried out in a sterile environment. Five to six week old mice maintained in clean rooms were used for bacterial clearance studies. Mice were anesthetized with a mixture of nitrous oxide and oxygen. The trachea was exposed through a midline incision and dissection through the thyroid gland. One hundred microliters of bacterial suspension was instilled into the trachea with a 27 gauge needle just below the cricoid cartilage. The two halves of the thyroid muscles were apposed at the midline and the skin incision was closed by approximating the two edges with surgical glue. Animals were housed for either 6 or 24 hours prior to sacrifice. Lungs and spleen tissues were harvested, weighed and homogenized in PBS. Dilutions of homogenized lung tissues and spleen were then plated on BAP. Plates were incubated overnight at 37° C.

After either 6 or 24 hours post infection, lungs from treated and control mice were harvested, weighed, homogenized in PBS and plated on BAP to evaluate formation of GBS colonies. The cultured plates were incubated at 37° C. for approximately 16–18 hours (overnight). Colony forming units per gram of lung tissue (CFU/g) were assessed by manual counting of bacterial colonies.

Figure 1:
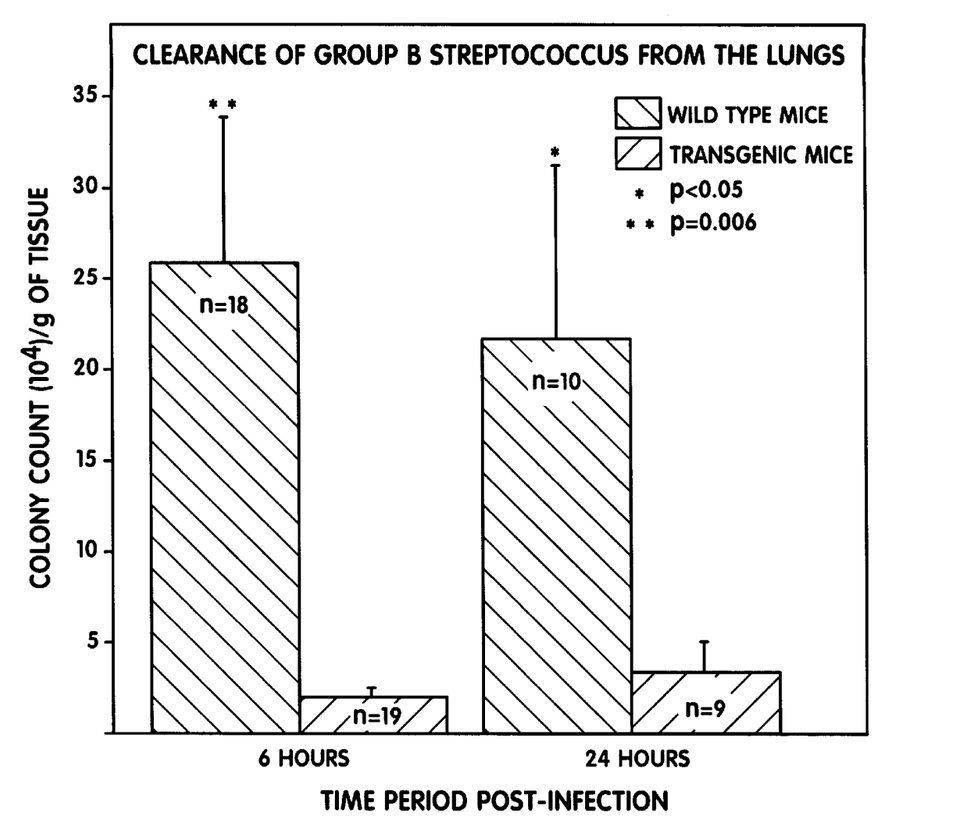
FIG. 1 is a graph showing bacterial clearance from lungs of transgenic (lysozyme/surfactant protein-B fusion protein) and control mice.

As shown in FIG. 1, transgenic mice harboring the chimeric protein SEQ ID NO:3 had significantly fewer CFU/g of lung tissue at both 6 hours and 24 hours following infection with GBS. The number of CFU in most transgenic mice was even less than the number of bacteria that had been administered. As shown in FIG. 1, transgenic mice had significantly enhanced clearance of GBS from the lungs at both the 6 h and 24 h post infection time points. At 6 h post-infection, BAP inoculated with lung tissue from transgenic (treated) mice had $1.99 \pm 1.4 \times 10^4$ CFU/g of tissue, while BAP inoculated with lung tissue from wild type (control) mice had $25.49 \pm 12.43 \times 10^4$ CFU/g ($p<0.006$). At 24 h post-infection, BAP inoculated with lung tissue from transgenic (treated) mice had $9.9 \pm 6.43 \times 10^4$ CFU/g tissue, while BAP inoculated with lung tissue from wild type (control) mice had $67.29 \pm 34.2 \times 10^4$ CFU/g tissue ($p<0.04$).

These results suggested that the expression of lysozyme/surfactant protein-B fusion protein SEQ ID NO:3 in the airway of the transgenic mice facilitated bacterial clearance from the airway. The results show that in mice carrying the lysozyme/surfactant protein-B fusion protein SEQ ID NO:3, bacterial proliferation was inhibited at 6 hours post infection, while bacterial clearance was enhanced at 24 hours post infection. Transgenic mice which expressed a lysozyme/surfactant protein B fusion protein SEQ ID NO:3 in the distal airway were twelve-fold more efficient in clearing bacteria in the airway than their wild type littermates. This lysozyme-produced efficacy is particularly striking, since wild type mice are inherently very efficient in clearing bacteria in the airway.

Two other lines of transgenic mice expressed the lysozyme/surfactant protein-B chimeric protein SEQ ID NO:3 although at lower levels. Bacterial clearance in these lines was correspondingly lower, although still significantly greater than that in wild type control mice. Lysozyme enzyme activity was increased 40% (relative to wild type littermates) in bronchoalveolar lavage fluid of the transgenic line expressing the highest levels of the lysozyme/SP-B fusion protein SEQ ID NO:3. Since bacterial clearance was enhanced twelve-fold in this line, the antibacterial effect may have been conferred by the SP-B C-terminal propeptide with the preceding amino acids from the mature peptide SEQ ID NO:4 alone, or the result of the combined action of SP-B and lysozyme SEQ ID NO:3 components; alternatively the effect may be due to increased lysozyme SEQ ID NO:1 activity.

The lysozyme/SP-B fusion protein SEQ ID NO:3 or SEQ ID NO:6 of the invention may be used to treat and/or reduce bacterial colonization of the airway. The latter use would be extremely beneficial in treating individuals with cystic fibrosis, since chronic bacterial colonization of the major airways with consequent debilitating exacerbations is the major cause of the morbidity and mortality suffered by cystic fibrosis patients.

Cystic fibrosis is a systemic disease in which mucus secretion is altered so that a viscid mucus is produced. Production of altered mucus leads to dilation of the exocrine ducts, destruction of acinar tissue, and replacement of the destroyed tissue by fibrous connective tissue. Involvement of the lungs leads to pneumonia and bronchiectasis. These patients often succumb at a young age to terminal lung infections with *Pseudomonas aeruginosa* in spite of aggressive antibiotic therapy. Therefore, the bactericidal activity of lysozyme or the lysozyme/surfactant protein-B fusion protein in vivo offers a potential therapeutic strategy for suppressing bacterial colonization of the airways in cystic fibrosis patients without compromising whatever degree of respiratory function the patient exhibits.

It will be appreciated that prophylaxis or treatment by the method and composition of the invention may range from total prevention, reduction of the bacterial load, amelioration of the severity of, or elimination of a bacterial infection. The lysozyme/SP-B fusion protein SEQ ID NO:3 or SEQ ID NO:6 may be used to protect against all bacterial strains which colonize the respiratory tract such as, for example, *Staphylococcus aureus*, Streptococcus species, *Streptococcus pneumoniae, Neisseria meningitidis, Neisseria gonorrhoeae,* Klebsiellae species, Proteus species, *Pseudomonas cepacia, Haemophilus influenzae, Bordetella pertussis, Mycoplasma pneumoniae, Legionella pneumophila*.

Additionally, the invention may be used to combat gastrointestinal infections. The lysozyme/surfactant protein-B fusion protein SEQ ID NO:3 or SEQ ID NO:6 may be administered by an enteral route to target the gastrointestinal tract for treating or preventing infections with bacterial strains that colonize the gastrointestinal tract such as, for example, Salmonellae species, Shigellae species, *Escherichia coli*, and Vibrio species, *Yersinia enterocolitica, Campylobacter fetus*, ssp. *jejune*, and *Helicobacter pylon*. The lysozyme/SP-B may be formulated for oral administered as a solid or liquid in the form of a capsule, tablet, syrup, and so on.

Other variations or embodiments of the invention will also be apparent to one of ordinary skill in the art from the above description. For example, other fusion proteins besides surfactant protein-B, such as members of the structurally related saposin protein family such as saposin A, saposin B, saposin C, saposin D, NK lysin, pore forming peptide of amoebapore A etc., could be generated. Various modes of administration besides inhalation could be used, such as injection, etc. The fusion protein SEQ ID NO:3 or SEQ ID NO:6 may be administered either alone or in combination with antibiotic therapy. Thus, the forgoing embodiments are not to be construed as limiting the scope of this invention.

What is claimed is:

1. A composition comprising a lysozyme/surfactant protein-B fusion protein selected from the group consisting of SEQ ID NO:3 and SEQ ID NO:6.

2. The composition of claim 1 for prophylaxis or treatment of a bacterial infection in a mammal.

3. The composition of claim 2 for prophylaxis or treatment of a respiratory bacterial infection.

4. The composition of claim 3 wherein said respiratory infection is in said mammal having cystic fibrosis.

5. The composition of claim 2 for prophylaxis or treatment of a gastrointestinal infection.

6. A method of prophylaxis or treating a bacterial infection in a mammal comprising administering a lysozyme/surfactant protein-B fusion protein selected from the group consisting of SEQ ID NO:3 and SEQ ID NO:6 in a pharmaceutically acceptable carrier to said mammal at a dose sufficient to prevent or treat the infection.

7. The method of claim 6 wherein said fusion protein is administered by a method selected from the group consisting of a parenteral and a nonparenteral method.

8. The method of claim 6 wherein the parenteral method is by inhalation.

9. A fusion protein selected from the group consisting of SEQ ID NO:3 and SEQ ID NO:6 having antibacterial activity in a mammal.

10. A method of treating a bacterial respiratory infection in an individual having cystic fibrosis comprising administering a lysozyme/surfactant protein-B fusion protein selected from the group consisting of SEQ ID NO:3 and SEQ ID NO:6 to said individual.

11. The method of claim 10 wherein the administration is by a parenteral route.

12. The method of claim 10 wherein the fusion protein administration is by aerosol installation.

* * * * *

UNITED STATES PATENT AND TRADEMARK OFFICE
CERTIFICATE OF CORRECTION

PATENT NO. : 5,993,809
DATED : November 30, 1999
INVENTOR(S) : Timothy Edward Weaver, et al.

It is certified that error appears in the above-identified patent and that said Letters Patent is hereby corrected as shown below:

Column 2,
Line 64, "a rat" should be -- a human --

Column 3
Line 3, "Iysozyme/SP-B" should be -- lysozyme/SP-B --
Line 55, "poly A30" should be -- poly $A^+$ --

Column 4,
Line 7, "Iysozyme/surfactant-B" should be -- lysozyme/surfactant-B --
Line 52, "strain IIII" should be -- strain III --

Column 5,
Lines 4-8, delete: "Lungs and spleen tissues were harvested, weighed and homogenized in PBS. Dilutions of homogenized lung tissues and spleen were then plated on BAP. Plates were incubated overnight at 37° C."

Column 6,
Line 28, "Iysozyme/SP-B" should be -- lysozyme/SP-B --
Line 48, "jejune" should be -- jejuni -- and "pylon" should be -- pylori --

Column 11,
Line 46, "Human and Human" should be -- Human --

Signed and Sealed this

Eighteenth Day of September, 2001

Attest:

NICHOLAS P. GODICI
Attesting Officer   Acting Director of the United States Patent and Trademark Office

SEQUENCE LISTING

<160> NUMBER OF SEQ ID NOS: 6

<210> SEQ ID NO 1
<211> LENGTH: 148
<212> TYPE: PRT
<213> ORGANISM: RAT

<400> SEQUENCE: 1

Met Lys Ala Leu Leu Val Leu Gly Phe Leu Leu Ser Ala Ser Val
1               5                   10                  15

Gln Ala Lys Ile Tyr Glu Arg Cys Gln Phe Ala Arg Thr Leu Lys Arg
                20                  25                  30

Asn Gly Met Ser Gly Tyr Tyr Gly Val Ser Leu Ala Asp Trp Val Cys
            35                  40                  45

Leu Ala Gln His Glu Ser Asn Tyr Asn Thr Gln Ala Arg Asn Tyr Asn
    50                  55                  60

Pro Gly Asp Gln Ser Thr Asp Tyr Gly Ile Phe Gln Ile Asn Ser Arg
65                  70                  75                  80

Tyr Trp Cys Asn Asp Gly Lys Thr Pro Arg Ala Lys Asn Ala Cys Gly
                85                  90                  95

Ile Pro Cys Ser Ala Leu Leu Gln Asp Asp Ile Thr Gln Ala Ile Gln
                100                 105                 110

Cys Ala Lys Arg Val Val Arg Asp Pro Gln Gly Ile Arg Ala Trp Val
                115                 120                 125

Ala Trp Gln Arg His Cys Lys Asn Arg Asp Leu Ser Gly Tyr Ile Arg
        130                 135                 140

Asn Cys Gly Val
145

<210> SEQ ID NO 2
<211> LENGTH: 381
<212> TYPE: PRT
<213> ORGANISM: HUMAN
<220> FEATURE:
<221> NAME/KEY: PROPEP
<222> LOCATION: (0)...(0)

<400> SEQUENCE: 2

Met Ala Glu Ser His Leu Leu Gln Trp Leu Leu Leu Leu Pro Thr
1               5                   10                  15

Leu Cys Gly Pro Gly Thr Ala Ala Trp Thr Thr Ser Ser Leu Ala Cys
                20                  25                  30

Ala Gln Gly Pro Glu Phe Trp Cys Gln Ser Leu Glu Gln Ala Leu Gln
            35                  40                  45

Cys Arg Ala Leu Gly His Cys Leu Gln Glu Val Trp Gly His Val Gly
    50                  55                  60

Ala Asp Asp Leu Cys Gln Glu Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
                100                 105                 110

Asn Gln Val Leu Asp Asp Tyr Phe Pro Leu Val Ile Asp Tyr Phe Gln
                115                 120                 125

Asn Gln Ile Asp Ser Asn Gly Ile Cys Met His Leu Gly Leu Cys Lys
        130                 135                 140

-continued

```
Ser Arg Gln Pro Glu Pro Glu Gln Glu Pro Gly Met Ser Asp Pro Leu
145                 150                 155                 160

Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
            180                 185                 190

Thr Gln Asp Leu Ser Glu Gln Gln Phe Pro Ile Pro Leu Pro Tyr Cys
        195                 200                 205

Trp Leu Cys Arg Ala Leu Ile Lys Arg Ile Gln Ala Met Ile Pro Lys
    210                 215                 220

Gly Ala Leu Arg Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met Asp Asp Ser Ala Gly Pro Arg Ser Pro
        275                 280                 285

Thr Gly Glu Trp Leu Pro Arg Asp Ser Glu Cys His Leu Cys Met Ser
    290                 295                 300

Val Thr Thr Gln Ala Gly Asn Ser Ser Glu Gln Ala Ile Pro Gln Ala
305                 310                 315                 320

Met Leu Gln Ala Cys Val Gly Ser Trp Leu Asp Arg Glu Lys Cys Lys
                325                 330                 335

Gln Phe Val Glu Gln His Thr Pro Gln Leu Leu Thr Leu Val Pro Arg
            340                 345                 350

Gly Trp Asp Ala His Thr Thr Cys Gln Ala Leu Gly Val Cys Gly Thr
        355                 360                 365

Met Ser Ser Pro Leu Gln Cys Ile His Ser Pro Asp Leu
    370                 375                 380

<210> SEQ ID NO 3
<211> LENGTH: 260
<212> TYPE: PRT
<213> ORGANISM: Rat and Human
<220> FEATURE:
<223> OTHER INFORMATION: Chimeric Protein

<400> SEQUENCE: 3

Met Lys Ala Leu Leu Val Leu Gly Phe Leu Leu Leu Ser Ala Ser Val
1               5                   10                  15

Gln Ala Lys Ile Tyr Glu Arg Cys Gln Phe Ala Arg Thr Leu Lys Arg
            20                  25                  30

Asn Gly Met Ser Gly Tyr Tyr Gly Val Ser Leu Ala Asp Trp Val Cys
        35                  40                  45

Leu Ala Gln His Glu Ser Asn Tyr Asn Thr Gln Ala Arg Asn Tyr Asn
    50                  55                  60

Pro Gly Asp Gln Ser Thr Asp Tyr Gly Ile Phe Gln Ile Asn Ser Arg
65                  70                  75                  80

Tyr Trp Cys Asn Asp Gly Lys Thr Pro Arg Ala Lys Asn Ala Cys Gly
                85                  90                  95

Ile Pro Cys Ser Ala Leu Leu Gln Asp Asp Ile Thr Gln Ala Ile Gln
            100                 105                 110

Cys Ala Lys Arg Val Val Arg Asp Pro Gln Gly Ile Arg Ala Trp Val
        115                 120                 125
```

```
Ala Trp Gln Arg His Cys Lys Asn Arg Asp Leu Ser Gly Tyr Ile Arg
        130                 135                 140

Asn Cys Gly Val Val Cys Arg Leu Val Leu Arg Cys Ser Met Asp Asp
145                 150                 155                 160

Ser Ala Gly Pro Arg Ser Pro Thr Gly Glu Trp Leu Pro Arg Asp Ser
                165                 170                 175

Glu Cys His Leu Cys Met Ser Val Thr Thr Gln Ala Gly Asn Ser Ser
            180                 185                 190

Glu Gln Ala Ile Pro Gln Ala Met Leu Gln Ala Cys Val Gly Ser Trp
        195                 200                 205

Leu Asp Arg Glu Lys Cys Lys Gln Phe Val Glu Gln His Thr Pro Gln
        210                 215                 220

Leu Leu Thr Leu Val Pro Arg Gly Trp Asp Ala His Thr Thr Cys Gln
225                 230                 235                 240

Ala Leu Gly Val Cys Gly Thr Met Ser Ser Pro Leu Gln Cys Ile His
                245                 250                 255

Ser Pro Asp Leu
            260

<210> SEQ ID NO 4
<211> LENGTH: 112
<212> TYPE: PRT
<213> ORGANISM: Human
<220> FEATURE:
<221> NAME/KEY: PROPEP
<222> LOCATION: (0)...(0)
<223> OTHER INFORMATION: C-terminal propeptide + 10 amino acids of
      mature SP-B

<400> SEQUENCE: 4

Val Cys Arg Leu Val Leu Arg Cys Ser Met Asp Asp Ser Ala Gly Pro
1               5                   10                  15

Arg Ser Pro Thr Gly Glu Trp Leu Pro Arg Asp Ser Glu Cys His Leu
            20                  25                  30

Cys Met Ser Val Thr Thr Gln Ala Gly Asn Ser Ser Glu Gln Ala Ile
        35                  40                  45

Pro Gln Ala Met Leu Gln Ala Cys Val Gly Ser Trp Leu Asp Arg Glu
50                  55                  60

Lys Cys Lys Gln Phe Val Glu Gln His Thr Pro Gln Leu Leu Thr Leu
65                  70                  75                  80

Val Pro Arg Gly Trp Asp Ala His Thr Thr Cys Gln Ala Leu Gly Val
                85                  90                  95

Cys Gly Thr Met Ser Ser Pro Leu Gln Cys Ile His Ser Pro Asp Leu
            100                 105                 110

<210> SEQ ID NO 5
<211> LENGTH: 148
<212> TYPE: PRT
<213> ORGANISM: Human and Human
<220> FEATURE:

<400> SEQUENCE: 5

Met Lys Ala Leu Ile Val Leu Gly Leu Ala Leu Leu Ser Val Thr Val
1               5                   10                  15

Gln Gly Lys Val Phe Gly Arg Cys Glu Leu Ala Arg Thr Leu Lys Arg
            20                  25                  30

Leu Gly Met Asp Gly Tyr Arg Gly Ile Ser Leu Ala Asn Trp Met Cys
        35                  40                  45
```

```
Leu Ala Lys Trp Glu Ser Gly Tyr Asn Thr Arg Ala Thr Asn Tyr Asn
         50                  55                  60

Ala Gly Asp Arg Ser Thr Asp Tyr Gly Ile Phe Gln Ile Asn Ser Arg
 65                  70                  75                  80

Tyr Trp Cys Asn Asp Gly Lys Thr Pro Gly Ala Val Asn Ala Cys His
                 85                  90                  95

Leu Ser Cys Ser Ala Leu Leu Gln Asp Asn Ile Ala Asp Ala Ala Ala
                100                 105                 110

Cys Ala Lys Arg Val Val Arg Asp Pro Gln Gly Val Arg Ala Trp Ala
                115                 120                 125

Ala Trp Arg Asn Arg Cys Gln Asp Arg Asp Val Arg Gln Tyr Val Gln
        130                 135                 140

Gly Cys Gly Val
145

<210> SEQ ID NO 6
<211> LENGTH: 260
<212> TYPE: PRT
<213> ORGANISM: Human and Human
<220> FEATURE:
<223> OTHER INFORMATION: Chimeric Protein

<400> SEQUENCE: 6

Met Lys Ala Leu Ile Val Leu Gly Leu Ala Leu Leu Ser Val Thr Val
 1               5                  10                  15

Gln Gly Lys Val Phe Gly Arg Cys Glu Leu Ala Arg Thr Leu Lys Arg
                 20                  25                  30

Leu Gly Met Asp Gly Tyr Arg Gly Ile Ser Leu Ala Asn Trp Met Cys
             35                  40                  45

Leu Ala Lys Trp Glu Ser Gly Tyr Asn Thr Arg Ala Thr Asn Tyr Asn
         50                  55                  60

Ala Gly Asp Arg Ser Thr Asp Tyr Gly Ile Phe Gln Ile Asn Ser Arg
 65                  70                  75                  80

Tyr Trp Cys Asn Asp Gly Lys Thr Pro Gly Ala Val Asn Ala Cys His
                 85                  90                  95

Leu Ser Cys Ser Ala Leu Leu Gln Asp Asn Ile Ala Asp Ala Ala Ala
                100                 105                 110

Cys Ala Lys Arg Val Val Arg Asp Pro Gln Gly Val Arg Ala Trp Ala
                115                 120                 125

Ala Trp Arg Asn Arg Cys Gln Asp Arg Asp Val Arg Gln Tyr Val Gln
        130                 135                 140

Gly Cys Gly Val Val Cys Arg Leu Val Leu Arg Cys Ser Met Asp Asp
145                 150                 155                 160

Ser Ala Gly Pro Arg Ser Pro Thr Gly Glu Trp Leu Pro Arg Asp Ser
                165                 170                 175

Glu Cys His Leu Cys Met Ser Val Thr Thr Gln Ala Gly Asn Ser Ser
                180                 185                 190

Glu Gln Ala Ile Pro Gln Ala Met Leu Gln Ala Cys Val Gly Ser Trp
        195                 200                 205

Leu Asp Arg Glu Lys Cys Lys Gln Phe Val Glu Gln His Thr Pro Gln
210                 215                 220

Leu Leu Thr Leu Val Pro Arg Gly Trp Asp Ala His Thr Thr Cys Gln
225                 230                 235                 240
```

```
Ala Leu Gly Val Cys Gly Thr Met Ser Ser Pro Leu Gln Cys Ile His
            245                 250                 255
Ser Pro Asp Leu
            260
```